(12) United States Patent
Brooks et al.

(10) Patent No.: US 8,858,469 B2
(45) Date of Patent: Oct. 14, 2014

(54) DETERMINING THE OFFSET OF THE HEAD PART OF AN ORTHOPAEDIC JOINT PROSTHESIS STEM COMPONENT

(75) Inventors: James Brooks, Leeds (GB); Andrew Burton, Leeds (GB)

(73) Assignee: Depuy International Limited (GB)

( * ) Notice: Subject to any disclaimer, the term of this patent is extended or adjusted under 35 U.S.C. 154(b) by 1147 days.

(21) Appl. No.: 12/597,971

(22) PCT Filed: Mar. 18, 2008

(86) PCT No.: PCT/GB2008/000948
§ 371 (c)(1),
(2), (4) Date: Feb. 19, 2010

(87) PCT Pub. No.: WO2008/132424
PCT Pub. Date: Nov. 6, 2008

(65) Prior Publication Data
US 2010/0191339 A1     Jul. 29, 2010

(30) Foreign Application Priority Data

Apr. 28, 2007    (GB) .................................. 0708264.7
Dec. 12, 2007    (GB) .................................. 0724212.6

(51) Int. Cl.
*A61B 5/103*      (2006.01)
*A61B 5/117*      (2006.01)
(Continued)

(52) U.S. Cl.
CPC ....... *A61F 2/4657* (2013.01); *A61F 2220/0033* (2013.01); *A61F 2002/30332* (2013.01); *A61F 2002/3652* (2013.01); *A61F 2/4637* (2013.01); *A61F 2002/30329* (2013.01); *A61F 2002/30617* (2013.01); *A61F 2/36* (2013.01); *A61F 2002/30802* (2013.01); *A61F 2002/365* (2013.01); *A61F 2220/0025* (2013.01); *A61F 2/3609* (2013.01); *A61F 2250/0089* (2013.01);
(Continued)

(58) Field of Classification Search
USPC ...................... 600/587; 606/102; 33/511, 512
See application file for complete search history.

(56) References Cited

U.S. PATENT DOCUMENTS 4,658,808 A *    4/1987    Link ......................... 623/16.11
4,959,066 A        9/1990    Dunn
(Continued)

FOREIGN PATENT DOCUMENTS

| EP | 1430859 A1 | 6/2004 |
|----|-----------|--------|
| WO | WO 9200045 A1 | 1/1992 |
| WO | WO 2004010382 A1 | 1/2004 |

OTHER PUBLICATIONS

PCT International Search Report and Written Opinion PCT/GB2008/000948 dated Jun. 12, 2008.

(Continued)

*Primary Examiner* — Devin Henson (57) ABSTRACT

A method of determining the offset of the head part of an orthopaedic joint prosthesis stem component, relative to the neck of the stem part on which the head part can be fitted, involves obtaining a first and second images of the patient's joint on a non-coincident first and second planes. Template parts are fitted to the first and second images of the bone, which have markings on them which can be placed relative to the head part and the stem part respectively of the patient's bone, and scales for measuring first and second displacements which are the distances between the axis of the head part and the axis of the neck of the patient's bone measured in the first and second planes.

17 Claims, 7 Drawing Sheets

(51) Int. Cl.
  *G01B 1/00*  (2006.01)
  *A61B 1/00*  (2006.01)
  *A61F 2/30*  (2006.01)
  *A61F 2/36*  (2006.01)
  *A61F 2/46*  (2006.01)
  *A61F 2/34*  (2006.01)
  *A61F 2/40*  (2006.01)

(52) U.S. Cl.
  CPC .............. *A61F 2002/30963* (2013.01); *A61F 2002/30714* (2013.01); *A61F 2002/4668* (2013.01); *A61F 2250/0097* (2013.01); *A61F 2/34* (2013.01); *A61F 2002/4623* (2013.01); *A61F 2002/30604* (2013.01); *A61F 2/40* (2013.01); *A61F 2002/30344* (2013.01); *A61F 2/4684* (2013.01); *A61F 2002/3619* (2013.01); *A61F 2002/3631* (2013.01); *A61F 2002/3625* (2013.01); *A61F 2002/3611* (2013.01)
  USPC .............................. 600/587; 33/511; 33/512

(56) References Cited

U.S. PATENT DOCUMENTS

| | | | |
|---|---|---|---|
| 5,342,366 A | | 8/1994 | Whiteside |
| 5,360,446 A | | 11/1994 | Kennedy |
| 5,792,143 A | * | 8/1998 | Samuelson et al. ........... 606/102 |
| 7,388,972 B2 | * | 6/2008 | Kitson ........................ 382/128 |
| 2003/0181831 A1 | | 9/2003 | Tanaka |
| 2006/0204067 A1 | | 9/2006 | Tuma |

OTHER PUBLICATIONS

UK Search Report 0708264.7 dated Jul. 19, 2007.

\* cited by examiner

DETERMINING THE OFFSET OF THE HEAD PART OF AN ORTHOPAEDIC JOINT PROSTHESIS STEM COMPONENT

The present application is a continuation of International Patent Application PCT/GB2008/000948 filed Mar. 18, 2008.

BACKGROUND OF THE INVENTION

This invention relates to a method of determining the offset of the head part of an orthopaedic joint prosthesis stem component, relative to the neck of the stem part on which the head part can be fitted, and to a template kit for use in such a method.

Modular stem components of an orthopaedic joint prosthesis can comprise a stem part which can be fitted into a prepared cavity in a long bone, and a head part which has an articulating surface for articulation with the opposed bearing surface patient's anatomic joint, or with the bearing surface of another component of the joint prosthesis. Such prostheses can be used in, for example, the replacement of hip joints and of shoulder joints.

The stem component can extend into the medullary canal of the bone (which might be the femur or the humerus). The stem component will define a neck axis. The neck is directed towards the other component of the joint prosthesis when the prosthesis is implanted. The head part of the prosthesis is fitted on to the neck of the stem part. The stem part can have an intramedullary portion and a neck portion. As is known, the angle between the intramedullary and neck portions is usually between about 30° and about 50°, to match the anatomy of the patient. For some applications, the stem component can have a neck portion which sits in the neck region of the patient's bone, without an intramedullary portion.

The head part can have a bearing surface which provides for articulation with a corresponding bearing surface of the mating component of the joint prosthesis. The bearing surface of the head part can be convex, for articulation with a concave bearing surface of the mating component. This will frequently be the arrangement in the case of a hip joint prosthesis and can also be the arrangement in the case of a shoulder joint prosthesis. The bearing surface of the head part can be concave, for articulation with a convex bearing surface of the mating component, as can be the arrangement in the case of shoulder joint prostheses, sometimes referred to as reversed shoulder joint prostheses.

It can be preferred for the axis of the head part to be offset relative to the axis of the neck of the stem part of a joint prosthesis component. This can facilitate matching the configuration of the component to the patient's anatomy. Varying the offset in the plane which is perpendicular to the anterior-posterior axis can affect the effective length of the patient's limb. Varying the offset in the plane which is perpendicular to the medial-lateral axis can affect the degree of retroversion or anteversion in the replacement joint.

BRIEF SUMMARY OF THE INVENTION

The present invention provides a technique for determining the offset of the head part of an orthopaedic joint prosthesis stem component, relative to the neck of the stem part on which the head part can be fitted, using images of the patient's bone which are obtained in two non-coincident planes in which the angle between the planes is known.

Accordingly, in one aspect, the invention provides a method of determining the offset of the head part of an orthopaedic joint prosthesis stem component, relative to the neck of the stem part on which the head part can be fitted, which comprises:
 a. obtaining a first image of the patient's joint on a first plane,
 b. obtaining a second image of the patient's joint on a second plane, in which the planes are non-coincident and in which the angle between the planes is known;
 c. fitting a template part to the first image of the bone, in which the template part has markings on it which can be placed relative to the head part and the stem part respectively of the patient's bone, and a scale on it for use when measuring the first displacement which is the distance between the axis of the head part and the axis of the neck of the patient's bone measured in the first plane,
 d. fitting a template part to the second image of the bone, in which the template part has markings on it which can be placed relative to the head part and the stem part respectively of the patient's bone, and a scale on it for use when measuring the second displacement which is the distance between the axis of the head part and the axis of the neck of the patient's bone measured in the second plane,
 e. using reference data to calculate from the first and second displacements the $r, \theta$ coordinates of the axis of the head part relative to the axis of the neck of the stem part, where r is the absolute distance between the axis of the head part and the axis of the neck of the stem part, and $\theta$ is a measure of the angular location of the axis of the head part around the axis of the neck of the stem part.

The technique that is provided by the present invention provides information relating to the amount of the offset of the axis of the head part relative to the axis of the neck of the stem part, and relating to the orientation of that offset around the axis of the neck of the stem part. These parameters can be used conveniently when assembling head and stem parts, whether of a trial component or of an implant component.

The technique of the invention is particularly useful when assembling a modular stem component which comprises a stem part and a head part, and a connector which can be used to connect the head part to the stem part, in which the head part has an eccentric recess within it in which the connector can be received, and the connector has an eccentric recess within it in which a spigot on the stem part can be received. The combination of the eccentric connection between the stem part and the connector and the eccentric connection between the connector and the head part enables a range of configurations of the assembled prosthesis component to be obtained, with a range of offset displacements between the axis of the stem part and the polar axis of the head part, and the possibility of the direction through which the axes are offset being at a range of angles relative to, say, the plane which contains the neck axis and the intramedullary axis of the stem part.

UK patent application no. 0705905.8 discloses a trial instrument which can be used in a surgical procedure to implant a modular stem component of the type discussed above. The instrument comprises:
 a. a head part which corresponds to the head of an orthopaedic joint component, in which the head part has a bore formed in it,
 b. a connector for connecting the head part to a stem part of the orthopaedic joint component, which is intended for location in the intramedullary cavity of a bone, in which the connector can be fitted into the bore in the head part in one of a plurality of angular orientations, and in which the connector comprises a body part and a trigger which can be moved relative to the body part between an unlocked position in which the connector can be moved relative to the head part between different ones of the plurality of angular orientations and a locked position in which the connector is restrained against such movement.

The technique of the present invention is applicable to the assembly of the instrument which is disclosed in UK patent application no. 0705905.8. Subject matter that is disclosed in the specification of that application is incorporated in the specification of the present application by this reference.

The angle between the first and second planes will generally be at least about 80°. The angle between the first and second planes will generally be not more than about 100°. Preferably, the angle between the first and second planes is about 90°.

Preferably, the first image is created in the plane which is perpendicular to the anterior-posterior axis.

Preferably, the second image is created in the plane which is perpendicular to the medial-lateral axis.

Preferably, the first image or the second image or each of them is an X-ray image. It is envisaged that alternative imaging techniques might be used, for example computer tomography techniques.

The images which are used in the technique of the invention can be printed, for example on film. The templates can be printed on a sheet of material, so that the printed images and the printed templates can be manipulated physically.

The technique of the invention can also be implemented using images which are displayed electronically, for example on a monitor. The templates can be printed and manipulated manually relative to the electronically displayed images. The templates displayed electronically and manipulated on the same monitor, for example using computer pointer hardware such as a mouse.

The reference data enables coordinate data for the offset of the head part relative to the neck of the stem part, which is obtained in the form of two displacement measurements, to be translated into coordinate data in the form of a displacement measurement and an angular measurement. This requires that the angle between the planes of the first and second images to be known. It can be preferred that the angle between the planes is 90 E. The translation of the coordinate data can be performed using trigonometry.

The present invention provides reference data to facilitate the translation of the coordinate data. The reference data can be provided in the form of a printed chart. It could also be obtained using a computer program. For example, a computer can be programmed to prompt for the coordinate data in the form of two displacement measurements, and then to manipulate that coordinate data to generate new coordinate data in the form of a displacement measurement and an angular measurement.

It will sometimes be convenient for a common template part to be fitted to the first and second images of the bone. This can be appropriate when the shapes of the head part in the first and second planes are generally the same.

A template part which is used in the technique of the present invention can have on it which are intended to represent the head part of the prosthesis component (which term is used in this context also to refer to a component of an instrument), which can be placed over the image of the head of the patient's bone in one of the images. For example, the template part can have on it an outline of a part-spherical body, with a radius which corresponds approximately to the radius of the head part of an implant component (or of a trial instrument which is intended to represent an implant component). It can be appropriate to provide a surgeon with a plurality of template parts, on which the head parts are depicted with different sizes.

A template part which has on it a representation of the head part of a prosthesis component can include scale which can be placed relative to the axis of the neck of the patient's bone, to provide an indication of the distance between the axis of the head and the axis of the neck of the patient's bone. The scale might comprise a plurality of parallel lines (which might be solid or broken), which can be aligned so that they are arranged approximately parallel to the axis of the neck of the patient's bone, as identified previously by analysis of the image of the bone.

Preferably, the representation of the head part, and the scale which is placed relative to the neck of the patient's bone, are provided on a common component. However, it is envisaged that the template part might comprise more than one piece, in which the representation of the head part is provided on one piece and the scale is provided on the other piece. The scale might be provided on either of the pieces of the two piece template.

Preferably, the method includes the steps of (a) aligning a head part and a stem part of an orthopaedic joint component according to the coordinates which are determined in step (e) of the method, and (b) connecting the head part to the stem part. The head part and the stem part can be parts of a trial instrument. The head part and the stem part can be parts of a joint prosthesis which are to be implanted in the patient.

Preferably, the orthopaedic joint prosthesis comprises a connector for connecting the head part to a stem part, in which the head part has an eccentric recess in it for receiving the connector, and the connector has an eccentric connection feature for connection to the stem part.

It can be preferred to use an alignment guide in the aligning step, the aligning guide having a recess formed in it in which the neck of the stem part can be received, and markings on it by which the angular location of the axis of the head part around the axis of the neck of the stem part can be estimated. Preferably, the alignment guide has a marking on it which provides a point of reference relative to a feature on the stem part or on the patient's bone.

Preferably, the method includes a step of fitting a stem template part to at least one of the first and second images of the bone for use in locating the axis of the neck of the stem part. The stem template part can have printed on it an outline of a stem part of the joint prosthesis component. Such stem template parts are known, and are used commonly to identify the appropriate size or position or both of a stem part of a prosthesis component, relative to the neck of the patient's bone, and to the intramedullary canal when the stem part extends into the intramedullary canal. The stem template part can have a line on it which indicates the location and orientation of the axis of the neck of the stem part when implanted in a patient.

Accordingly, in another aspect, the invention provides a template kit for use in a method of determining the offset of the head part of an orthopaedic joint prosthesis stem component, relative to the neck of the stem part on which the head part can be fitted, which comprises:

a. a first template part which has markings on it which represent the axis of the head of the patient's bone,    b. a second template part which has markings on it which represent the axis of the neck of the patient's bone,    c. a scale which is provided on at least one of the first and second template parts for use when measuring the distance between the axis of the head part and the axis of the neck of the patient's bone, d. a source of reference data which can provide, based on two such measured distances, the r,θ coordinates of the axis of the head part relative to the axis of the neck of the stem part, where r is the absolute distance between the axis of the head part and the axis of the neck of the stem part, and θ is a measure of the angular location of the axis of the head part around the axis of the neck of the stem part.

The method of the invention can include the step of assembling a head part and a stem part, in which the distance between the axis of the head part and the axis of the neck of the stem part, and the angular location of the axis of the head part around the axis of the neck component, are as determined in step (e) of the method. The head and stem parts can be parts of an implant. The head and stem parts can be parts of an instrument, for example of the kind which is the subject of UK patent application no. 0705905.8 discussed above.

The template parts which are used in the technique of the invention should be provided on a material which is capable of withstanding the conditions which are encountered when in use. Preferably, the material should be capable of withstanding exposure to fluids without degradation. The material should generally be at least partially transparent so that features of an X-ray image on which the template is place are visible through the template. It will often be preferred that the material is flexible.

Preferably, the material is a polymeric material. An example of a suitable material might include an acetate material.

When the representation of the neck axis is referenced against a plurality of parallel lines (which might be solid or broken), it can be appropriate for them to be differentiated from one another, for example by colour coding, or by different line patterns (such as, for example, lines which are solid, or broken such as when made up of a plurality of dashes or dots or a combination thereof).

When the reference data are provided in a printed chart, the material on which the data are printed should be capable of withstanding the conditions which are encountered when in use. Preferably, the material should be capable of withstanding exposure to fluids without degradation. Preferably, the material is a polymeric material. It might be transparent. However, for many applications, this will not be necessary.

In another aspect, the invention provides a method of assembling a joint prosthesis component, which comprises:
  a. obtaining a first image of the patient's joint on a first plane,
  b. fitting a template part to the first image of the bone, in which the template part has markings on it which can be placed relative to the head part and the stem part respectively of the patient's bone, and a scale on it for use when measuring the first displacement which is the distance between the axis of the head part and the axis of the neck of the patient's bone measured in the first plane,
  c. providing a head part of a joint prosthesis and a connector for connecting the head part to a stem part, in which the head part has an eccentric recess in it for receiving the connector, and the connector has an eccentric connection feature for connection to the stem part,
  d. locating the connector in the recess in the head part, and aligning it to provide a desired offset with reference to the displacement measurement obtained in step (a).

Embodiments of the invention will now be described by way of example with reference to the accompanying drawings, in which.

BRIEF DESCRIPTION OF THE DRAWINGS

DETAILED DESCRIPTION OF THE INVENTION

Figure 1:
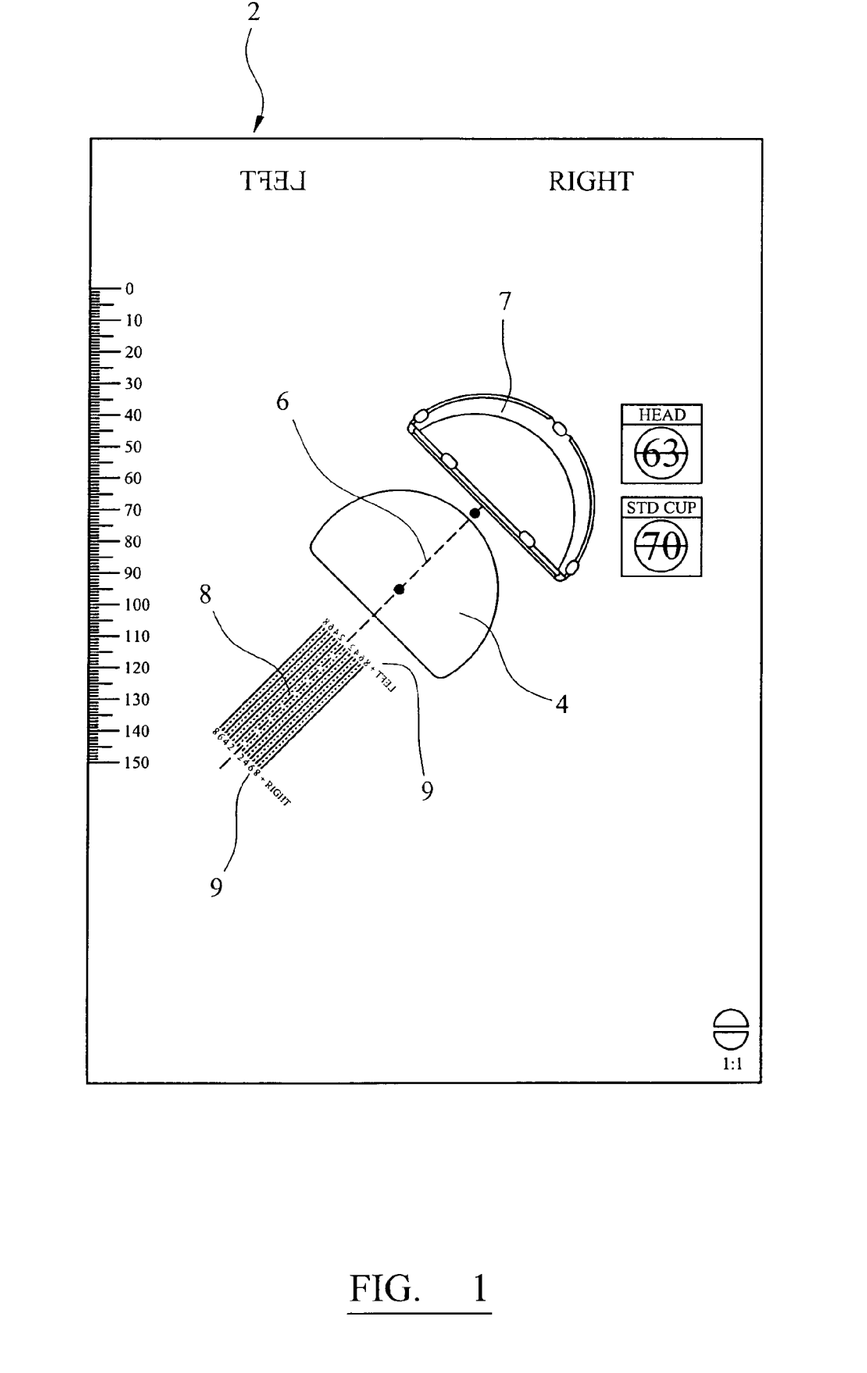
FIG. 1 is a representation of a first template part which can be used in the technique of the invention.

Referring to the drawings, FIG. 1 shows a template part 2 which comprises a sheet of a transparent acetate material, having markings on it. The markings are provided in an indelible material, which is resistant to degradation on exposure to body fluids and to cleaning fluids, and to treatments which might be employed during cleaning (such as exposure to elevated temperatures or to radiation).

A first marking 4 represents the head part of a femoral component of a joint prosthesis. It has a part-circular outline, which is truncated on a line which is perpendicular to the axis 6 of the head.

A second marking 7 represents the cup component of a hip joint prosthesis, for use when both stem and cup components of the joint prosthesis are to be implanted. The representation of the cup component can be disregarded when the bearing surface of the head part of the femoral component articulates with opposed bearing surface patient's anatomic joint.

The template part 2 has a series 8 of parallel lines on it, which extend parallel to the axis 6 which is defined by the first marking 4. Two scales 9 are provided against the parallel lines, representing the distance in millimeters between various ones of the parallel lines and the axis 6 which is defined by the first marking 4. It can be preferred for the lines on one side of the axis to be printed in a colour which is different from the lines on the other side of the axis. It can be preferred for the scale on one side of the axis to be printed in a colour which is different from the scale on the other side of the axis. For example the lines or the scale or each of them on one side of the axis might be printed in black. The lines or the scale or each of them on one side of the axis might be printed in red. The provision of two scales enables the template part to be used in relation to replacement of a right hip or a left hip, by reversal of the template (that is, turning the template over).

Figure 2:
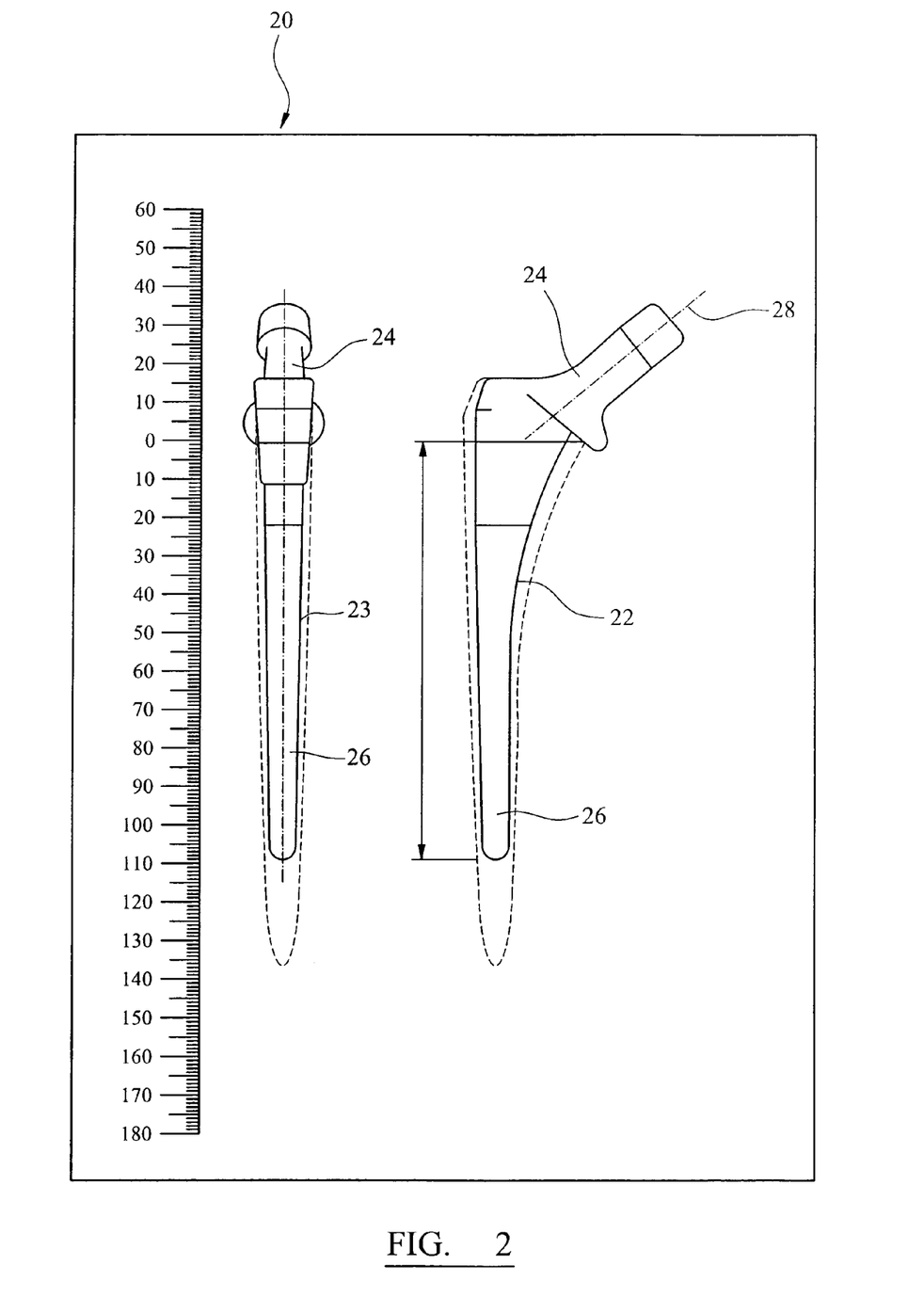
FIG. 2 is a representation of a second template part which can be used in the technique of the invention.

FIG. 2 shows a second template part 20 which comprises a sheet of a transparent acetate material, having markings on it. The markings are provided in an indelible material, which is resistant to degradation on exposure to body fluids and to cleaning fluids, and to treatments which might be employed during cleaning (such as exposure to elevated temperatures or to radiation).

A first marking 22 is an outline of the stem part of a femoral component of a hip joint prosthesis, viewed along the anterior-posterior axis, showing the neck portion 24 and the intramedullary portion 26. The axis 28 of the neck portion is marked on the template part.

A second marking 23 is an outline of the stem part of a femoral component of a hip joint prosthesis, viewed along the medial-lateral axis, showing the neck portion 24 and the intramedullary portion 26.

Figure 3:
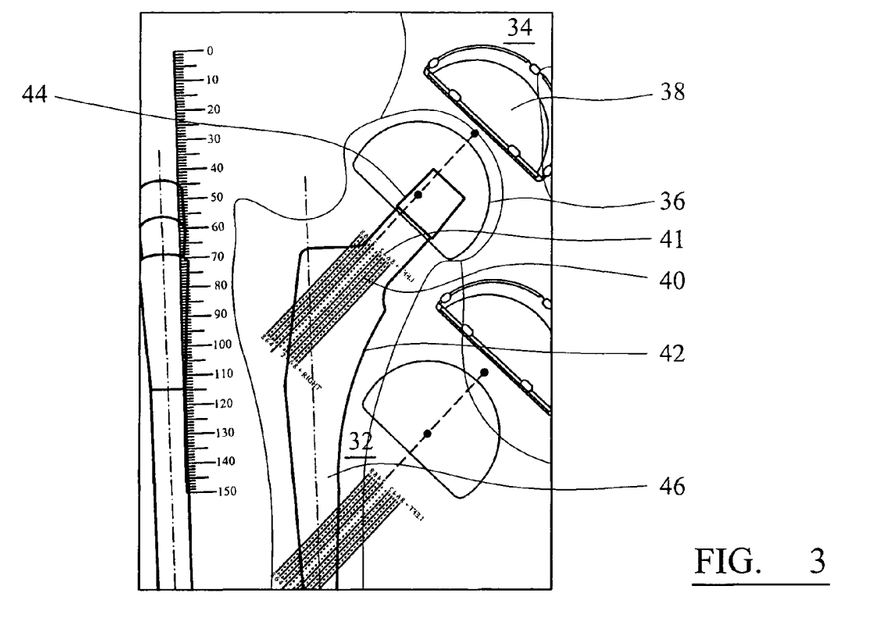
FIG. 3 shows the template parts shown in FIGS. 1 and 2 superimposed over an X-ray image of a patient's proximal femur in a first plane which is perpendicular to the anterior-posterior axis.

FIG. 3 shows an X-ray image of a patient's hip joint, in the plane which is perpendicular to the anterior-posterior axis. The image shows the outline 32 of the patient's femur and the outline 34 of the patient's pelvis.

A first template is shown, positioned on the X-ray image. The first template has printed on it a first marking 36 which represents the head part of a femoral component of a hip joint prosthesis, and a second marking 38 represents the cup component of a hip joint prosthesis. It also has printed on it a series 40 of parallel lines on it, which extend parallel to the axis which is defined by the first marking 36. Two scales 41 are provided against the parallel lines, representing the distance in millimeters between various ones of the parallel lines and the axis which is defined by the first marking 36. The first template therefore has printed on it the markings which are on the template shown in FIG. 1.

The first template is positioned so that the circumferential edge defined by the first marking 36 is aligned with the bearing surface of the head of the patient's femur.

A second template is shown, positioned on the X-ray image. The second template has printed on it an outline 42 of the stem part of the femoral component of a hip joint prosthesis, viewed along the anterior-posterior axis. The outline has a neck portion 44 and an intramedullary portion 46. The second template is positioned so that the intramedullary portion of the outline is positioned appropriately relative to the cortical bone which defines the intramedullary cavity in the patient's femur. Its position along the intramedullary axis of the bone is adjusted so that the neck portion of the outline is positioned appropriately relative to the cortical bone in the neck of the patient's femur. The second template includes a marking which indicates the position of the axis of the neck portion of the outline.

The positions of the first and second templates are such that the axis of the head part on the first template and the axis of the neck portion of the stem part on the second template are parallel. The scale on the first template can then be used to measure the distance between the parallel axes, with reference to the closest of the series 40 of parallel lines on the first template to the axis of the neck portion on the second template. This distance (the "first distance") is recorded.

Figure 4:
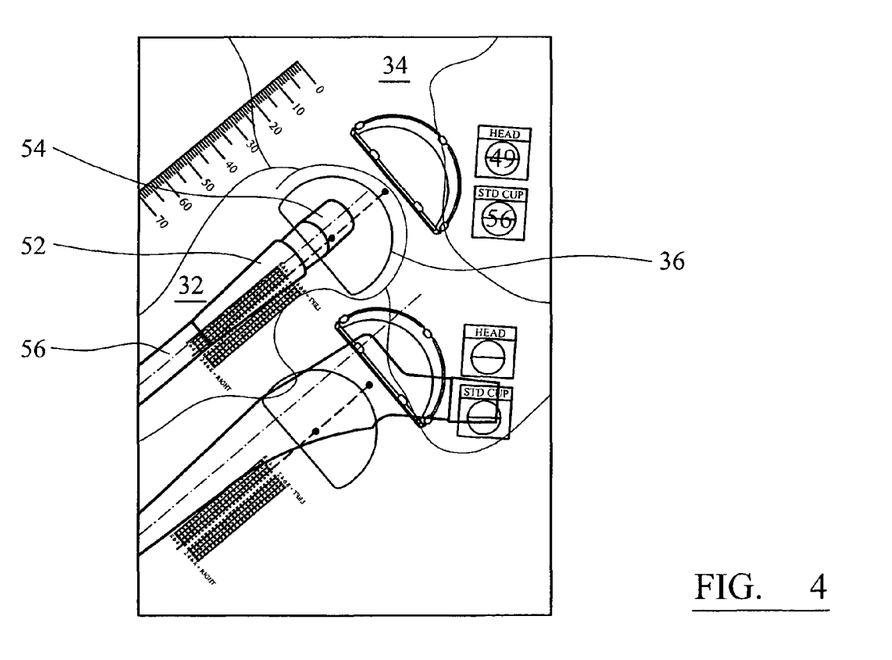
FIG. 4 shows the template parts shown in FIGS. 1 and 2 superimposed over an X-ray image of a patient's proximal femur in a second plane which is perpendicular to the medial-lateral axis.

FIG. 4 shows a second X-ray image of a patient's hip joint, in the plane which is perpendicular to the anterior-posterior axis. The image shows the outline 32 of the patient's femur and the outline 34 of the patient's pelvis.

A first template is shown, positioned on the X-ray image. The first template which is shown in FIG. 4 is the same as the first template which is shown in FIG. 3. The first template is positioned so that the circumferential edge defined by the first marking 36 is aligned with the bearing surface of the head of the patient's femur.

A second template is shown, positioned on the X-ray image. The second template has printed on it an outline 52 of the stem part of the femoral component of a hip joint prosthesis, viewed along the medial-lateral axis. The outline has a neck portion 54 and an intramedullary portion 56. The second template is positioned so that the intramedullary portion of the outline is positioned appropriately relative to the cortical bone which defines the intramedullary cavity in the patient's femur. Its position along the intramedullary axis of the bone is adjusted so that the neck portion of the outline is positioned appropriately relative to the cortical bone in the neck of the patient's femur. The second template includes a marking which indicates the position of the axis of the neck portion of the outline.

The positions of the first and second templates are such that the axis of the head part on the first template and the axis of the neck portion of the stem part on the second template are parallel. The scale on the first template can then be used to measure the distance between the parallel axes, with reference to the closest of the series 40 of parallel lines on the first template to the axis of the neck portion on the second template. This distance (the "second distance") is recorded.

Figure 5:
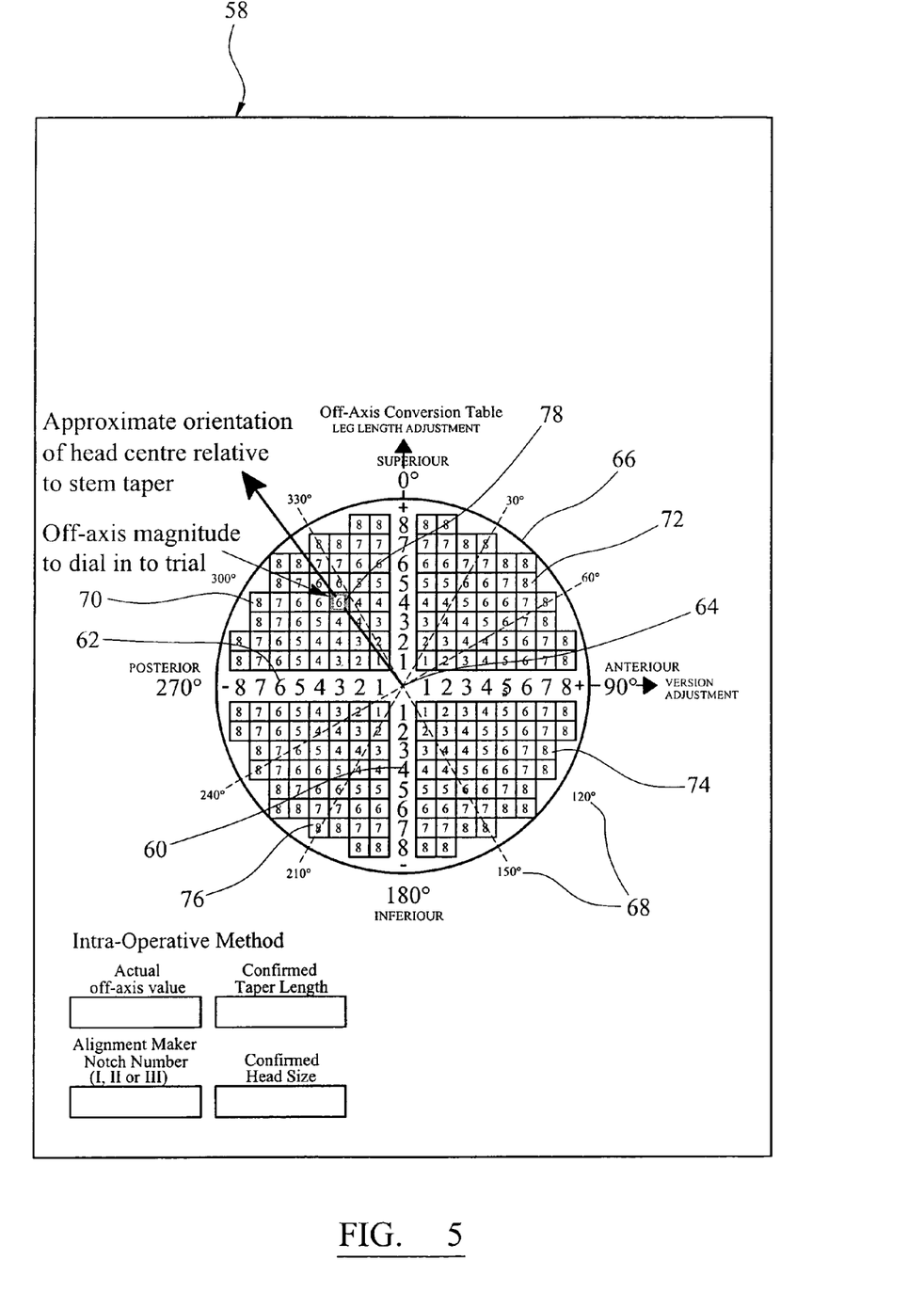
FIG. 5 is a representation of a chart which contains reference data, on which markings have been made.

FIG. 5 shows a printed chart which has a first axis 60 and a second axis 62 which intersect at an origin 64, within a circular outline 66. An angle scale 68 is printed around the periphery of the circular outline. Each of the axes 60, 62 has on it a series of numbers. These correspond to the first and second distances measured as described above with reference to FIGS. 4 and 5. The markings on the first axis 60 correspond to the measurements made with reference to the X-ray image viewed along the anterior-posterior axis, described above with reference to FIG. 4. The markings on the second axis 62 correspond to the measurements made with reference to the X-ray image viewed along the medial-lateral axis, described above with reference to FIG. 5.

Four series 70, 72, 74, 76 of displacement measurements are provided, in respective ones of the four quadrants between the first and second axes 60, 62.

In use, the displacement measurement which is applicable to a patient's implant is identified at the point 78 within one of the quadrants at which lines perpendicular to the first and second axes 60, 62 at points which correspond to the measured first and second distances intersect. In the example shown in FIG. 5, the measurement on the first axis 60 is "+4" and the measurement on the second axis is "−3". The calculated displacement measurement is "−5".

The angular location of the axis of the head part around the axis of the neck part is measured off the angle scale 68, with reference to a line which extends from the origin 54 through the point 78 at which lines perpendicular to the first and second axes 60, 62 at points which correspond to the measured first and second distances intersect. In the example shown in FIG. 5, the calculated angle is about 320°.

Figure 6:
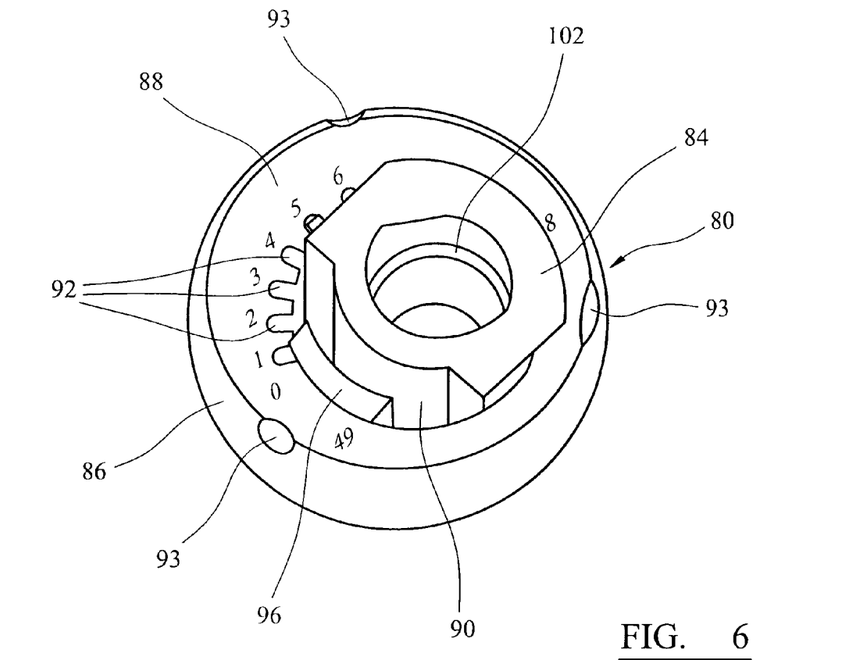
FIG. 6 is a view from below of a trial instrument which can be used to select the appropriate offset in an assembled femoral component.
Figure 7:
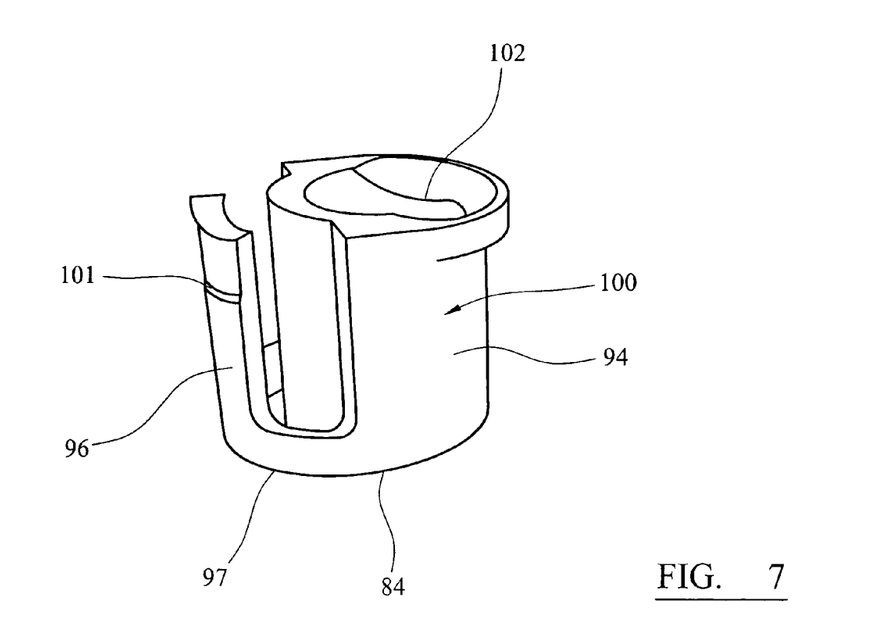
FIG. 7 is a side view of the connector of the trial instrument which is shown in FIG. 6.

FIG. 6 shows an instrument 80 which can be used to trial the head part (with its connector) on an implanted stem part. The instrument comprises a trial head part 82 and a trial connector 84. The trial connector is shown in FIG. 7. The trial head part has a spherical outer surface 86 which corresponds to the bearing surface of the head part of the ultimate implant, and an opposite reverse face 88. The head part has a recess 90 within it extending inwardly from the reverse face towards the bearing surface. The recess is generally round. The recess has a plurality of grooves 92 in its side wall extending parallel to the axis of the recess. Each of the grooves has a numerical marking against it. The numerical markings correspond to the range of the displacement measurements which are indicated in the four quadrants of the chart shown in FIG. 5. The trial head part can be formed from a metal such as a stainless steel or from a polymeric material.

The spherical outer surface 86 of the trial head part has three notches 93 at spaced apart points. The notches are distinguishable from one another, for example by means of distinguishing markings located adjacent to the notches.

The trial connector 84 is formed from a polymeric material. It comprises a body part 94 and a trigger 96 which is connected to the body part at one end 97. The material of the trigger 96, and of the body part when the trial connector is formed as a single piece) is sufficiently resilient that the trigger can be deformed inwardly towards the body part.

The body part has a rib 100 which is dimensioned so that it can fit into one of the grooves 92 in the side wall of the recess.

The trial head part and the trial connector have locking features so that the connector is retained within the recess 90 in the head part when the trigger is released, and can be removed from within the recess when the trigger is deformed towards the body part. The locking features can comprise an annular groove which extends around the recess, and a rib 101 on one or each of the body part and the trigger of the trial connector. When the rib is received in the groove, the trial connector is locked against removal from the bore in the trial head part. When the trigger 96 is squeezed towards the body part 94, the trial connector is able to move transversely within the recess in the body part so that the rib can be withdrawn from the groove, allowing the trial connector to be withdrawn from within the recess.

The body part 94 of the trial connector has a bore 102 formed in it. The bore is tapered inwardly in a direction away from the bottom face of the connector. The bore is open at its opposite narrow end. The bore is blind at its narrow end. The bore 102 in the trial connector is sized so that a tapered spigot on the neck of a stem component is a snug fit within it.

In use, the displacement measurement which is obtained using the templates and reference data chart as described above with reference to FIGS. 1 to 5 can be transferred to the trial instrument shown in FIG. 6 by locating the rib 100 on the connector in the appropriate groove 72 which is indicated by a marking which corresponds to the displacement measurement.

FIG. 7 shows the head part 110 of a femoral component of a hip joint prosthesis according to the present invention. The head part has a spherical bearing surface 112 and an opposite reverse face 114. The spherical bearing surface extends through an angle of arc of about 200 E. The radius of the bearing surface is 18 mm. The distance from the reverse face of the head part to the point where the polar axis intersects the bearing surface is from 28.25 to 41.8 mm.

A tapered bore 116 is formed in the reverse face 114. The bore has a circular cross-section. At the reverse face, the diameter of the bore is from 24.2 to 28.6 mm. The depth of the bore, measured from the reverse face of the head part to the blind end of the bore, is from 9.0 to 11.5 mm. The angle between the wall of the bore and its axis (which is half of the angle defined by the diametrically opposite walls of the bore) is 5°.

The bore 116 is offset relative to the polar axis (which is the axis extending through the centre of the sphere defined by the bearing surface, perpendicular to the reverse face). The distance between the axis of the bore and the polar axis is from 2 to 4 mm.

The head part has a series of markings 117 on its reverse face. These relate to the distance through which the head part is offset relative to the axis of the stem part when the femoral component is assembled, as discussed below.

The head component has a chamfer surface 118 extending around its periphery where the chamfer and reverse faces come together. The chamfer surface is planar when the component is viewed in cross-section. The angle between the chamfer surface and the polar axis is about 50°. The chamfer surface has three markings 119 at spaced apart points. The markings are distinguishable from one another.

Figure 8:
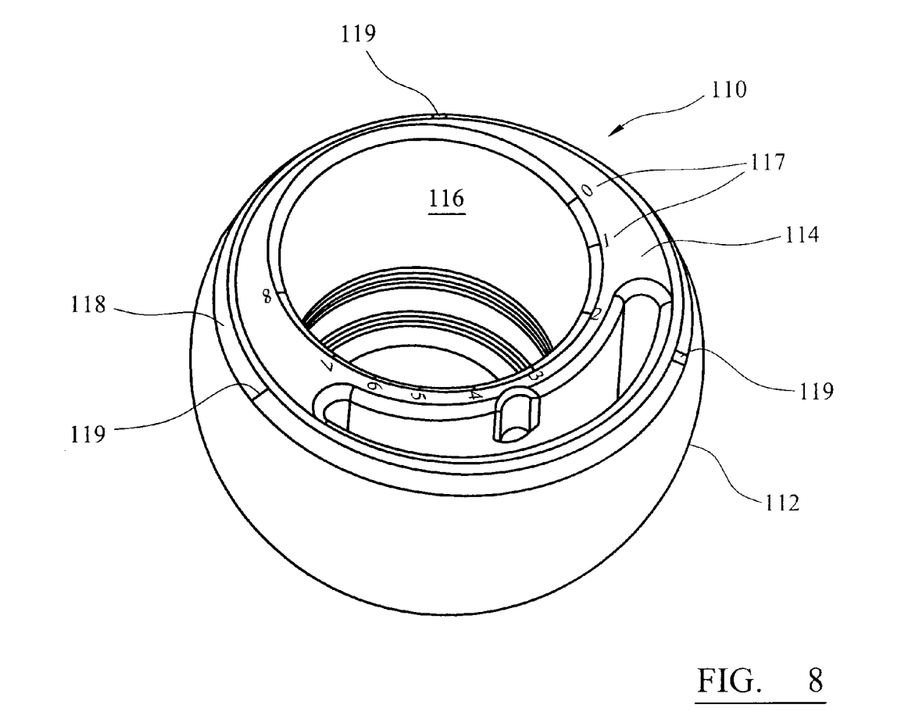
FIG. 8 is a view from below of a head part of a femoral component.
Figure 9:
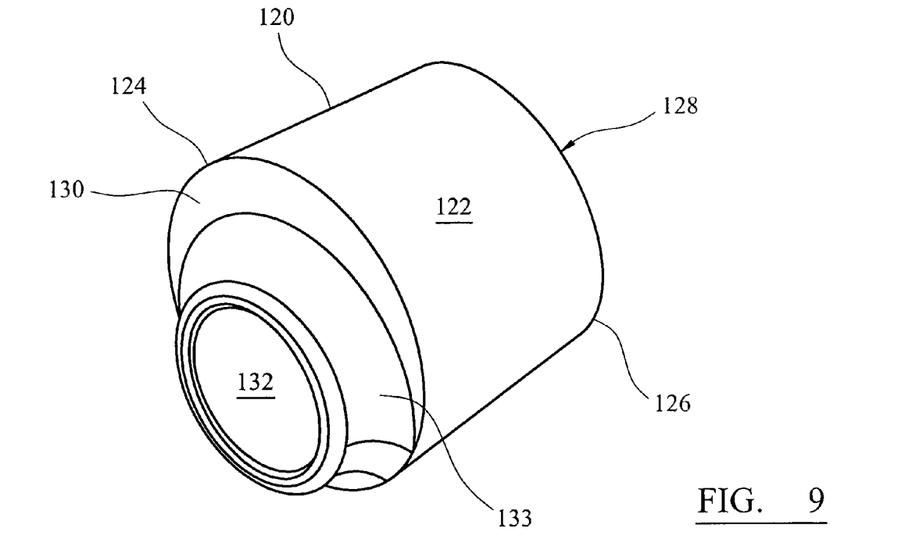
FIG. 9 is an isometric view from below of a connector in place which can be used to connect the head part shown in FIG. 8 to a stem part.

FIG. 8 shows a connector 120 which can be used to connect the head part to the neck of a stem part of a femoral component. The connector is circular when viewed from above and is tapered inwardly along the axis defined by its external surface 122. The diameter of the connector at its widest 124 point is from 24.2 to 28.3 mm. The diameter of the connector at its narrowest point 126 is from 22.45 to 20.7 mm. The depth of the connector measured from its top face 128 to its opposite bottom face 130 (not including the skirt which depends from the bottom face) is from 19.75 to 22.25 mm. The angle between the wall of the connector and its axis (which is half of the angle defined by the diametrically opposite walls of the connector) is 5°. The connector is therefore a snug fit in the bore 116 in the head part, with the top face 128 located within the bore 116 in the head part, and the bottom face 130 located adjacent to the reverse face 114 of the head part. When the connector is fully received in the bore 116 in the head part, the length of the contacting surfaces of the connector and the bore, measured along the axis of the bore, is from 19.75 to 22.25 mm. The widest point at which the connector is in contact with the bore is at the widest part of the connector part (that is at the bottom face 130). Accordingly, the ratio of the length of the contacting surfaces of the bore in the head part and the connector part when assembled, measured along the axis of the bore in the head part, to the diameter of the bore in the head part at the widest point at which it contacts the external surface of the connector part, is 1.23 (24.2:19.75) or 1.27 (28.3:22.25) in the two embodiments which are discussed.

The connector 120 has a bore 132 within it extending from the bottom face 130. The bore is tapered inwardly in a direction away from the bottom face of the connector. The bore is open at its opposite narrow end. The bore can be blind at its narrow end. A skirt 133 surrounds the bore at its open end on the bottom face 130.

The bore 132 in the connector is sized so that a spigot on the neck of a stem part is a snug fit within it.

In use, the displacement measurement which is obtained using the templates and reference data chart as described above with reference to FIGS. 1 to 5 can be transferred to the implant parts shown in FIGS. 7 and 8 with reference to the markings 117 on the reverse face of the head part and a corresponding alignment marker on the connector 120.

The trial head part can have markings on its external surface which indicate the direction around the axis of the head component in which the maximum offset is directed. One such marking is provided for each of the displacement measurements which are represented by the markings against the grooves 92 on the reverse face of the trial head part. The angular position of the trial head part relative to the implanted stem part angle can be set, using the angle data which is derived from the chart shown in FIG. 5 (as discussed above), by positioning the appropriate marking on the head component with an appropriate reference on the implanted stem, such as for example the medial-lateral axis of the stem.

A record of the angular orientation of the trial head part about the spigot on the neck of the implanted stem is made with reference to a selected one of the notches 93 on the spherical outer surface 86 of the trial head part, using a diathermy to make a mark on bone tissue immediately below the selected notch. This mark on the bone tissue can provide a point of reference for setting the angular orientation of the head part of the prosthesis component, using the mark on the bone tissue as a point of reference for a selected one of the markings 119 on the chamfer surface 118 of the head part.

Figures 10, 11A, 11B:
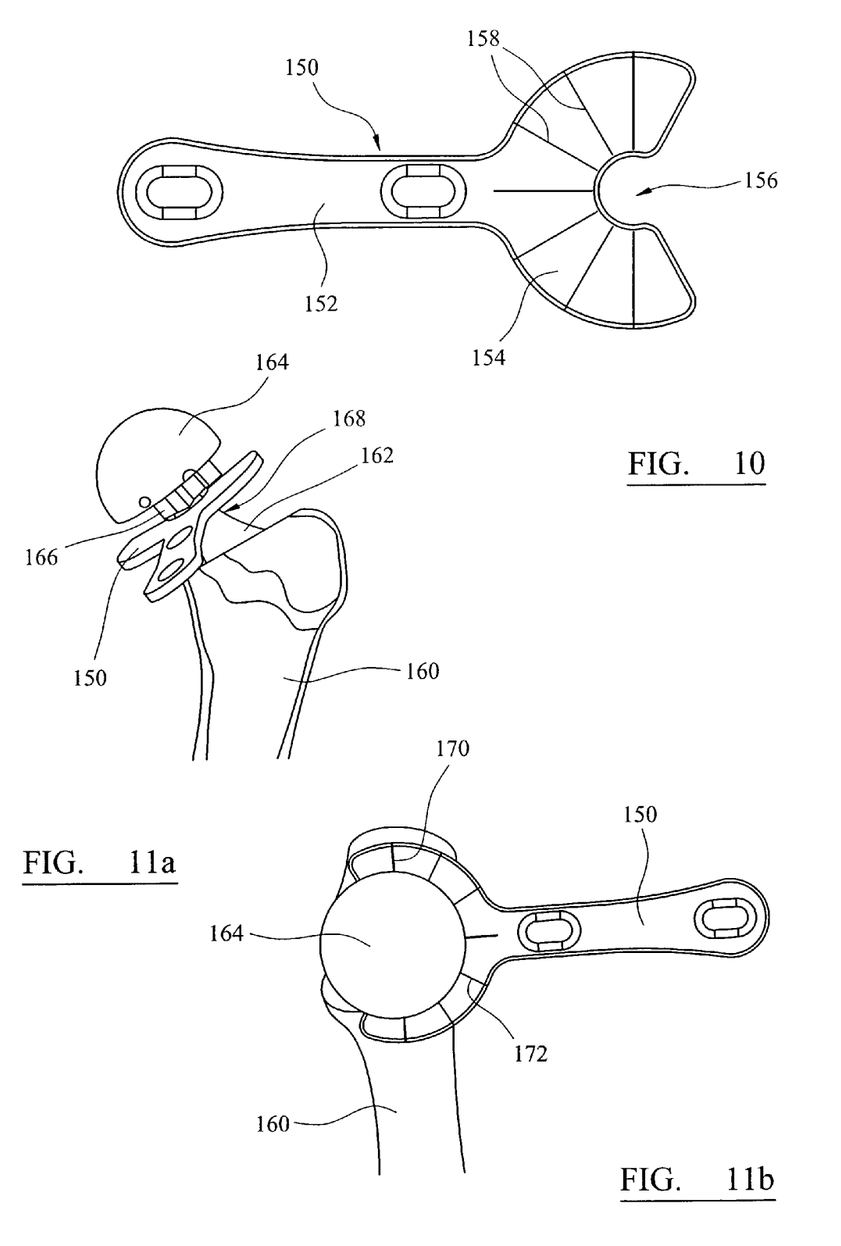
FIG. 10 is a plan view of an alignment guide which can be used to align a head part and a stem part of an orthopaedic joint prosthesis.
FIGS. 11a and 11b are views of the neck region of a patient's femur along the anterior posterior axis and the axis of the patient's femoral neck respectively, with an implanted stem part of a femoral component of a joint prosthesis, and an alignment guide as shown in FIG. 10 in use to align a trial head part of the femoral component.

FIG. 10 shows an alignment guide 150 which can be used to align the head and stem parts of an orthopaedic joint component. The head part and the stem part can be parts of a trial instrument. The head part and the stem part can be parts of a joint prosthesis which are to be implanted in the patient. It is formed from a sheet of material which is preferably resistant to damage when exposed to fluids. Polymeric materials such as polyesters and polyolefins can be suitable.

The guide comprises a handle part 152 and a marked part 154. The marked part 154 is generally rounded and has a notch 156 formed in it. A plurality of markings 158 are arranged on the marked part, extending radially from the centre of the notch. The notch is sized to receive the neck of the stem part.

The use of the alignment guide is shown in FIGS. 11a and 11b. FIG. 11a shows the neck region of a femur 160 with the stem part 162 of the femoral component of a hip joint prosthesis implanted in it. A trial head part 164 with a connector 166 is positioned on the protruding neck 168 of the stem part. The alignment guide 150 is positioned against the stem part, with the neck 168 of the stem part received in the notch 156 in the guide.

As shown in FIG. 11b, a first marking 170 on the alignment guide is aligned with the axis of the femur. A selected other marking 172 is then used to align the trial head part according to the appropriate angular offset that is calculated using the template based technique which is described above. For this purpose, the surgeon can use one or more of the notches 93 on the trial head part (see FIG. 6).

The invention has been described above in relation to a hip joint prosthesis. The invention is applicable to the replacement of other joints, including in particular a shoulder joint.

The invention claimed is:

1. A method of determining the polar offset of a head of an orthopaedic joint prosthesis relative to a neck of a stem to which the head can be connected for an implantation procedure involving a patient's joint, the orthopaedic joint prosthesis comprising a connector for connecting the head to a stem, wherein the head has an eccentric recess sized to receive the connector, and the connector has an eccentric connection feature for connection to the stem, comprising the steps of:

obtaining a first image of the patient's joint in a first plane;

obtaining a second image of the patient's joint in a second plane, wherein the planes are non-coincident and wherein an angle between the first plane and the second plane is known;

positioning a template having a scale and markings thereon to the first image of the bone relative to the head and the stem;

measuring a first displacement offset defined as the distance between the axis of the head and the axis of the neck of the patient's bone measured in the first plane;

positioning a template having a scale and markings thereon to the second image of the bone relative to the head and the stem;

measuring a second displacement offset defined as the distance between the axis of the head and the axis of the neck of the patient's bone measured in the second plane, wherein one of the first displacement offset and the second displacement offset is greater than zero; and determining, by using the first displacement offset and the second displacement offset and reference data, the polar offset of the axis of the head relative to the axis of the neck of the stem in terms of polar coordinates r and $\theta$, wherein r is a distance between the axis of the head and the axis of the neck of the stem, and $\theta$ is a measure of an angular location of the axis of the head around the axis of the neck of the stem.

2. The method of claim 1, wherein the angle between the first and second planes is at least about 80 degrees.

3. The method of claim 1, wherein the angle between the first and second planes is not more than about 100 degrees.

4. The method of claim 1, wherein the angle between the first and second planes is about 90 degrees.

5. The method of claim 1, wherein the first plane is perpendicular to the anterior-posterior axis.

6. The method of claim 1, wherein the second plane is perpendicular to the medial-lateral axis.

7. The method of claim 1, wherein the reference data are provided in a printed chart.

8. The method of claim 1, wherein the template used in the first positioning step is the same template used in the second positioning step.

9. The method of claim 1, wherein at least one of the positioning steps includes a step of using a stem template on at least one of the first and second images of the bone for use in locating the axis of the neck of the stem.

10. The method of claim 9, wherein the stem template has printed thereon an outline of a stem of the orthopaedic joint prosthesis.

11. The method of claim 1, further comprising the step of assembling a head and a stem, wherein the distance between the axis of the head and the axis of the neck of the stem, and the angular location of the axis of the head around the axis of the neck, are as determined in the determining step.

12. The method of claim 1, wherein the steps of obtaining images comprises obtaining the images using an X-ray imaging technique.

13. The method of claim 1, further comprising the steps of: aligning the head and the stem of an orthopaedic joint prosthesis according to the polar coordinates determined in the determining step; and connecting the head to the stem.

14. The method of claim 13, wherein the head and the stem are components of a trial instrument.

15. The method of claim 13, wherein the head and the stem are components of an implanted orthopaedic joint prosthesis.

16. The method of claim 13, wherein an alignment guide is used in the aligning step, the alignment guide having a recess formed therein, the recess configured to accept the neck of the stem, and markings thereon by which the angular location of the axis of the head around the axis of the neck of the stem can be estimated.

17. The method of claim 16, wherein the alignment guide has a marking thereon that provides a point of reference relative to a feature on the stem or on a bone of the patient's joint.

* * * * *